US010772599B2

(12) United States Patent
Merritt

(10) Patent No.: US 10,772,599 B2
(45) Date of Patent: Sep. 15, 2020

(54) DEVICES, SYSTEMS, AND METHODS FOR IN-STENT RESTENOSIS PREDICTION

(71) Applicant: VOLCANO CORPORATION, San Diego, CA (US)

(72) Inventor: Fergus Merritt, Escondido, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 980 days.

(21) Appl. No.: 14/964,287

(22) Filed: Dec. 9, 2015

(65) Prior Publication Data

US 2016/0166232 A1 Jun. 16, 2016

Related U.S. Application Data

(60) Provisional application No. 62/090,251, filed on Dec. 10, 2014.

(51) Int. Cl.
*A61B 8/12* (2006.01)
*A61B 8/08* (2006.01)
(Continued)

(52) U.S. Cl.
CPC .............. *A61B 8/12* (2013.01); *A61B 5/0084* (2013.01); *A61B 5/02007* (2013.01); *A61B 5/6853* (2013.01); *A61B 8/04* (2013.01); *A61B 8/06* (2013.01); *A61B 8/085* (2013.01); *A61B 8/0841* (2013.01); *A61B 8/0891* (2013.01); *A61B 8/46* (2013.01); *A61B 8/5223* (2013.01);
(Continued)

(58) Field of Classification Search
CPC . A61B 5/0084; A61B 5/02007; A61B 5/6853; A61B 8/04; A61B 8/06; A61B 8/0841; A61B 8/085; A61B 8/0891; A61B 8/12; A61B 8/445; A61B 8/46; A61B 8/5223; A61F 2/82; A61F 2/844; A61F 2/95
See application file for complete search history.

(56) References Cited

U.S. PATENT DOCUMENTS 6,200,268 B1   3/2001 Vince et al.
6,319,242 B1 * 11/2001 Patterson ........... A61B 17/3207
                                                    604/508
(Continued)

FOREIGN PATENT DOCUMENTS

JP         2006167287 A       6/2006

OTHER PUBLICATIONS

Bertrand et al. "Incidence of stent under-deployment as a cause of in-stent restenosis in long stents." International Journal of Cardiovascular Imaging 20: 279-284, 2004. (Year: 2004).*
(Continued)

*Primary Examiner* — Amelie R Davis

(57) ABSTRACT

Intravascular devices, systems, and methods are disclosed. In some instances, a method for treating a vessel of a patient includes collecting intravascular ultrasound imaging data of the placement of the stent using the intravascular ultrasound imaging device, estimating, using a processing device, a restenosis probability value based on the intravascular ultrasound imaging data of the placement of the stent and communicating the estimated restenosis probability value to a clinician. Associated devices and systems are also provided.

16 Claims, 8 Drawing Sheets

(51) Int. Cl.
  *A61B 8/00* (2006.01)
  *A61B 8/04* (2006.01)
  *A61B 5/00* (2006.01)
  *A61B 8/06* (2006.01)
  *A61B 5/02* (2006.01)
  *A61F 2/82* (2013.01)
  *A61F 2/844* (2013.01)
  *A61F 2/95* (2013.01)

(52) U.S. Cl.
  CPC ............... *A61F 2/82* (2013.01); *A61F 2/844* (2013.01); *A61F 2/95* (2013.01); *A61B 8/445* (2013.01)

(56) References Cited

U.S. PATENT DOCUMENTS

| | | | |
|---|---|---|---|
| 6,381,350 B1 | 4/2002 | Klingensmith et al. | |
| 7,074,188 B2 | 7/2006 | Nair et al. | |
| 7,175,597 B2 | 2/2007 | Vince et al. | |
| 7,215,802 B2 | 5/2007 | Klingensmith et al. | |
| 7,359,554 B2 | 4/2008 | Klingensmith et al. | |
| 7,463,759 B2 | 12/2008 | Klingensmith et al. | |
| 2001/0050087 A1 | 12/2001 | Weissman | |
| 2002/0077568 A1* | 6/2002 | Haddock | A61B 5/1076 600/587 |
| 2003/0100815 A1* | 5/2003 | Da Silva | A61B 5/02007 600/9 |
| 2006/0173299 A1* | 8/2006 | Romley | A61B 8/12 600/433 |
| 2007/0168019 A1* | 7/2007 | Amplatz | A61F 2/07 623/1.18 |
| 2009/0299175 A1 | 12/2009 | Bernstein | |
| 2011/0263936 A1* | 10/2011 | He | A61B 5/0066 600/109 |
| 2011/0306867 A1* | 12/2011 | Gopinathan | A61B 5/02007 600/407 |
| 2013/0046374 A1* | 2/2013 | Jones-McMeans | A61L 31/022 623/1.35 |
| 2013/0316487 A1 | 11/2013 | de Graff | |
| 2014/0163358 A1 | 6/2014 | Stigall | |
| 2014/0236011 A1 | 8/2014 | Fan | |
| 2014/0257087 A1* | 9/2014 | Elbasiony | A61B 5/061 600/424 |

OTHER PUBLICATIONS

Moussa, Issam et al "Does the Specific Intravascular Ultrasound Criterion used to Optimize Stent Expansion have an Impact on the Probability of Stent Restenosis", American Journal of Cardiology, vol. 83, No. 7, 1999, pp. 1012-1017.

De Feyter, P.J. et al "Reference Chart Derived from Post-Stent-Implantation Intravascular Ultrasound Predictors of 6-Month Expected Restenosis on Quantitative Coronary Angiography", Circulation, vol. 100, o. 17, 1999, pp. 1777-1783.

* cited by examiner

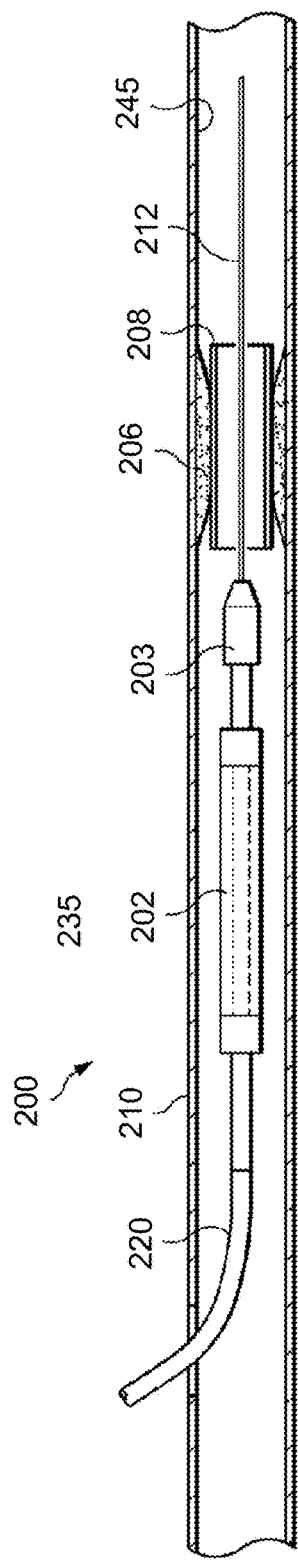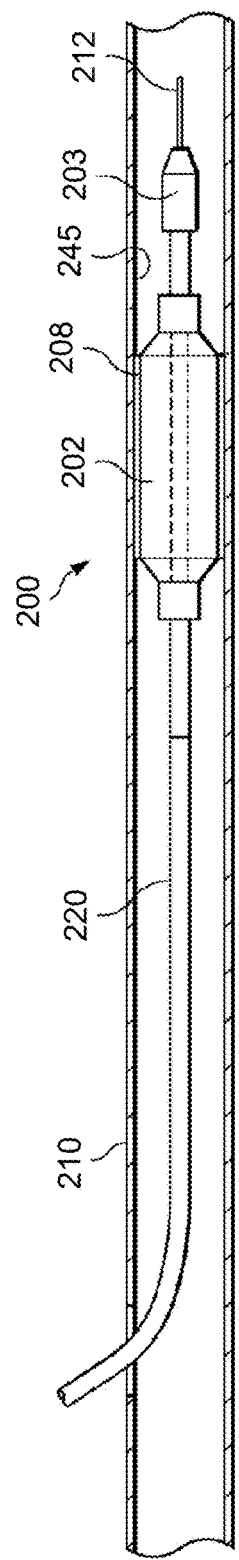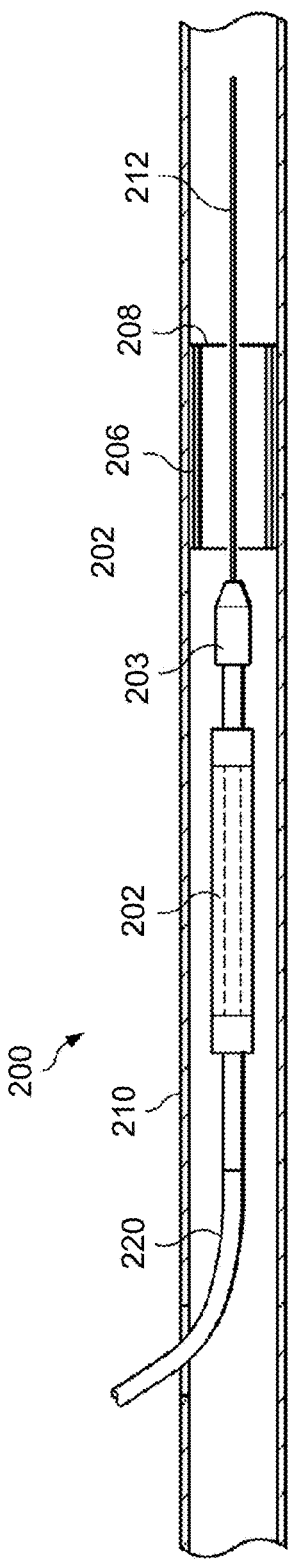

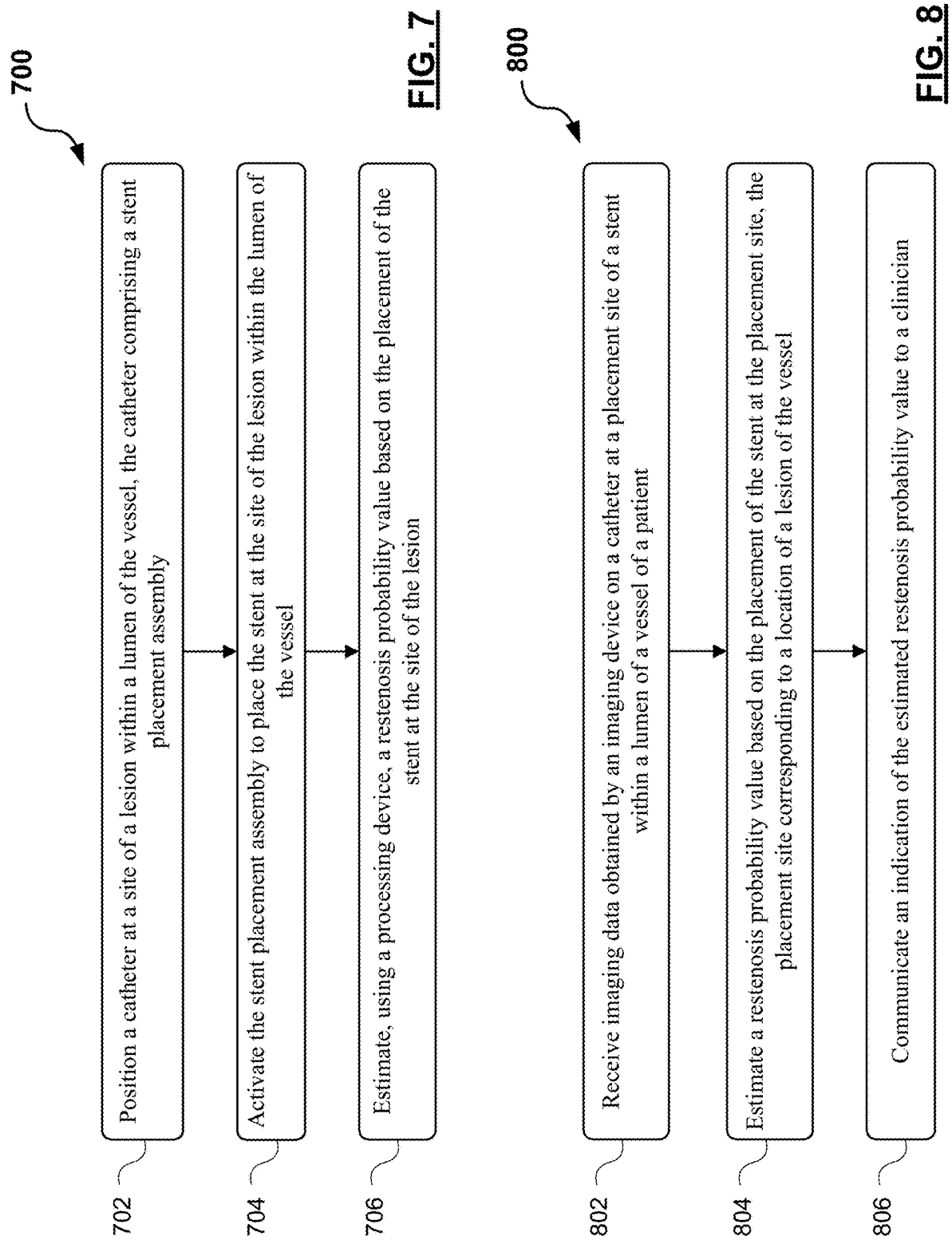

DEVICES, SYSTEMS, AND METHODS FOR IN-STENT RESTENOSIS PREDICTION

CROSS REFERENCE TO RELATED APPLICATIONS

The present application claims priority to and the benefit of the U.S. Provisional Patent Application No. 62/090,251, filed Dec. 10, 2014, which is hereby incorporated by reference in its entirety.

TECHNICAL FIELD

The present disclosure is generally related to the assessment of vessels, and in particular, to the assessment of the severity of blockage or other restrictions to the flow of fluid through a vessel, the treatment thereof, and the recurrence thereof.

BACKGROUND

Intravascular imaging systems and other intravascular physiology measurement systems are widely used in interventional cardiology as diagnostic tools for a diseased vessel, such as an artery, within the human body. Various sensors may be placed on a catheter and positioned in the body. One type of imaging system is an intravascular ultrasound (IVUS) system. In one example, a phased array IVUS device includes a number of transducers that are passed into a vessel and guided to an area to be imaged. The transducers emit ultrasonic waves in order to create an image of the vessel of interest. The ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Intravascular imaging systems are often used to detect arterial occlusions that can be relieved through use of a balloon catheter. A balloon catheter is a type of catheter with a balloon disposed near the tip. The balloon catheter is designed to be inserted into a patient's artery and positioned to a spot where an occlusion was detected through use of an intravascular imaging system. Upon reaching the detected occlusion, the balloon is inflated to compress the material causing the occlusion. In some instances, the balloon catheter is utilized to deploy a stent. In that regard, inflation of the balloon causes the stent to expand and deploy the stent within the vessel.

In some instances, an imaging system may be used to image the site of a stent in effort to observe, based on clinician experience, whether the placement of the stent is adequate. However, such current approaches have not been entirely satisfactory. Accordingly, there remains a need for improved devices, systems, and methods of objectively evaluating risk associated with and likelihood of success for one or more available treatment options for the vessel.

SUMMARY

The present disclosure provides devices, systems, and methods for assessing and treating an intravascular lesion and for assessing the efficacy of the treatment. As a result, the surgical process and treatment of the patient are improved by estimating the future performance of the treatment, which may be used to perform additional interventions right then, rather than in a subsequent medical procedure at a later time. Aspects of the present disclosure may reduce follow-up procedures and provide improved outcomes for the patients.

One general aspect includes a method of treating a vessel within a patient. The method includes inserting a catheter including a stent placement assembly and an intravascular ultrasound imaging device into a lumen of the vessel, positioning the catheter at a site of a lesion within the lumen of the vessel, activating the stent placement assembly to place the stent at the site of the lesion within the lumen of the vessel, and collecting intravascular ultrasound imaging data of the placement of the stent at the site of the lesion using the intravascular ultrasound imaging device disposed on the catheter. The method further includes estimating a restenosis probability value based on the intravascular ultrasound imaging data of the placement of the stent at the site of the lesion. The method also includes communicating the estimated restenosis probability value to a clinician.

Implementations may include one or more of the following features. The method further includes imaging a lumen of the vessel with the imaging device as the catheter is advanced or retracted through the vessel and identifying and imaging a lesion within the lumen of the vessel with the imaging device. The catheter includes the intravascular imaging device on a distal portion of the catheter. The estimating the restenosis probability value includes estimating the restenosis probability value based on at least one of a tissue type at the site, a plaque type at the site, a type of the stent, or location of the stent within the vessel.

One general aspect includes another method of treating a vessel within a patient. The method includes positioning a catheter at a site of a lesion within a lumen of the vessel, the catheter including a stent placement assembly, activating the stent placement assembly to place the stent at the site of the lesion within the lumen of the vessel, and estimating a restenosis probability value based on the placement of the stent at the site of the lesion.

Another general aspect includes a medical diagnosis and treatment system. The system includes a non-transitory, computer-readable medium to store instructions thereon and a processing device, in communication with the medium. The processing device executes the instructions to perform operations including receiving imaging data obtained by an imaging device on a catheter at a placement site of a stent within a lumen of a vessel of a patient and estimating a restenosis probability value based on the placement of the stent at the placement site, the placement site corresponding to a location of a lesion of the vessel. Some implementations of these aspects include corresponding computer systems, apparatus, and computer programs recorded on one or more computer storage devices coupled to one or more processing devices, each configured to perform or implement the actions of the methods.

Additional aspects, features, and advantages of the present disclosure will become apparent from the following detailed description.

BRIEF DESCRIPTIONS OF THE DRAWINGS

Illustrative embodiments of the present disclosure will be described with reference to the accompanying drawings, of which:

FIG. 1 is a diagrammatic view of a medical system for treating a vessel of a patient according to some embodiments of the present disclosure.

FIGS. 2A, 2B, 2C, 2D, 2E, and 2F are diagrams showing an illustrative insertion of a catheter into a vessel of a patient, according to embodiments of the present disclosure.

Figure 6:
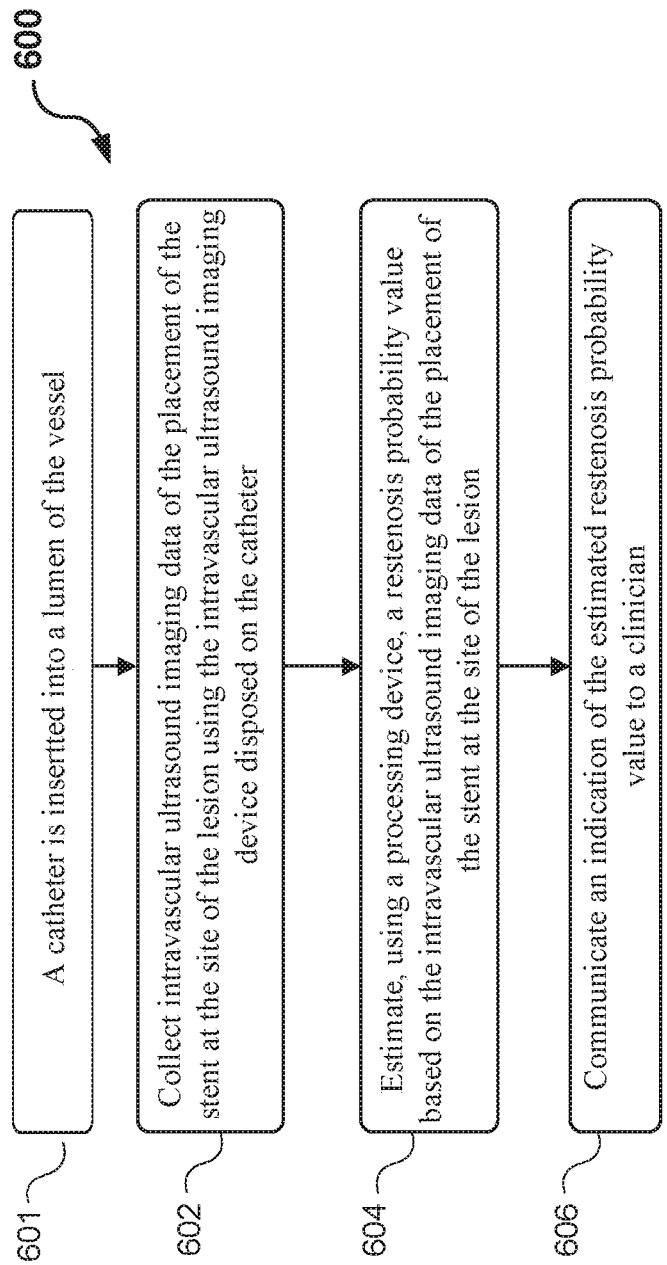

FIGS. 6, 7, and 8 are flow diagrams of methods of treating a vessel of the patient, according to some aspects of the present disclosure.

These accompanying drawings will be better understood by reference to the detailed description that follows.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
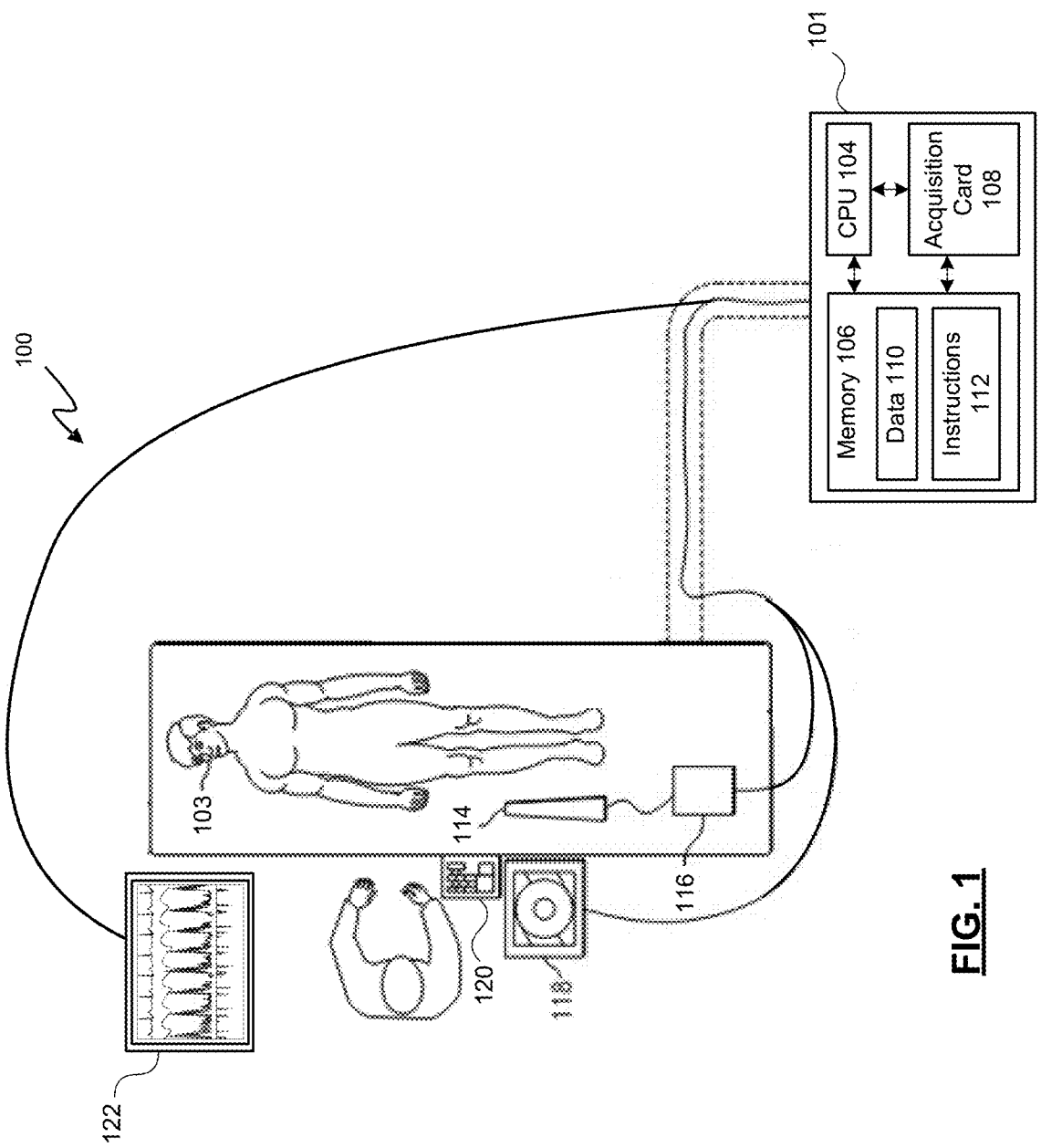

Referring now to FIG. 1, shown therein is a schematic diagram depicting a medical system 100. In general, the medical diagnosis and treatment system 100 or, simply, the medical system 100 provides for coherent acquisition, integration, and consolidation of multiple forms of acquisition and processing elements designed to be sensitive to a variety of modalities used to acquire and interpret human biological, physiology, and morphological information and to coordinate treatment of various conditions. In one embodiment, the medical system 100 includes a processing system 101 that is a computer system with the hardware and software to acquire, process, and display medical data and to facilitate control of one or more medical devices, such as intravascular devices. The processing system 101 may be a computer workstation that includes at least one processing device. Such as a micro controller or the depicted central processing unit (CPU) 104 and a non-transitory, computer-readable storage medium (illustrated as memory 106) such as a hard drive, random access-memory (RAM), flash memory, and/or compact disk read-only-memory (CD-ROM or DVD-ROM), etc. The processing system 101 may further include an acquisition card 108 to receive and/or process data from multiple medical device modalities. The acquisition card 108 may also provide an interface to communicate commands and requests to coupled medical devices. The memory 106 may include more than one memory or data storage device and may store data 110 acquired from coupled medical devices and instructions 112. The instructions 112 may include executable code that, when executed by the CPU 104 enables a user to view and interact with data received from coupled medical devices and/or data stored remotely and that enables a user to control the coupled medical devices. The instructions 112 include executable code to direct the processing system 101 to estimate a restenosis probability value based on information collected at the site of a lesion. In some embodiments, the instructions 112 include executable code to direct the medical system 100 to perform methods 600 and 700, 800 as described in detail further below. The processing system 101 may also include video controller such as a graphics processing unit (GPU), a speaker, and a network communication device such as an Ethernet controller or wireless communication controller.

In some embodiments, the processing system 101 is programmed to execute steps associated with the medical data acquisition, analysis, estimation, and control described herein. Accordingly, it is understood that any steps related to data acquisition, data processing, estimations based on acquired data, instrument control, and/or other processing or control aspects of the present disclosure may be implemented by the processing system 101 using corresponding instructions stored on or in a non-transitory, computer-readable medium accessible by the processing system.

In the depicted embodiment, the medical system 100 is deployed in a catheter lab having a control room, with the processing system 101 being located in the control room. In other embodiments, the processing system 101 may be located elsewhere, such as inside the catheter lab, in a centralized area in a medical facility, or at an off-site location accessible by an extended network. The catheter lab and control room may be used to perform on a patient any number of medical sensing and treatment procedures known in the art. A patient 103, depicted in catheter lab, may be undergoing a single modality or a multi-modality procedure either as a single procedure or in combination with one or more sensing procedures. For example, an angioplasty procedure may be performed to position a stent in a target location in a target region of the vasculature of the patient 103 having a lesion. The patient may be undergoing a percutaneous coronary intervention, performed by a clinician employing the processing system 101.

In the illustrated embodiment of FIG. 1, intravascular device 114 is a medical imaging device that may be utilized by a clinician to acquire medical imaging data about the patient 103 and/or to provide a treatment to the patient 103. For instance, the intravascular device 114 may obtain imaging data (including still images, video, etc.) by using ultrasound (e.g., IVUS), OCT, thermal, and/or other imaging techniques. The intravascular device 114 may be any form of device, instrument, catheter, guidewire, or probe that is sized and shaped to be positioned within a vessel. In some embodiments, intravascular device 114 may be combined with a non-imaging component into a single package that is sized and shaped to be positioned within a vessel. As illustrated, the IVUS intravascular device 114 is an IVUS catheter that includes one or more sensors such as a phased-array transducer to collect IVUS sensing data. In some embodiments, the intravascular device 114 may be capable of multi-modality sensing such as both IVUS and intravascular photoacoustic (IVPA) imaging, OCT imaging, pressure sensing, and flow sensing, etc.

In the depicted embodiment, a patient interface module (PIM) 116 couples the intravascular device 114 to the medical system 100. The PIM 116 facilitates the exchange of information between the intravascular device 114 and the processing system 101, serving as a medical device interface therebetween. The acquisition card 108 may provide communication between the CPU 104 and the intravascular device 114 by exchanging information with the PIM 116. This information includes imaging data transmitted from the intravascular device 114 to the processing system 101 and commands and settings, which may include individual parameter specifications, communicated from the processing system 101 to the PIM 116 and to the intravascular device 114 itself. Thus, the PIM 116 is operable to receive medical imaging and/or sensing data collected from the patient 103 using the intravascular device 114 and to transmit the received data to a processing system such as the processing system 101.

A bedside controller 118 is also communicatively coupled to the processing system 101 and provides user control of the particular medical modality (or modalities) being used to diagnose and/or treat the patient 103. In the current embodiment, the bedside controller 118 is a touch screen controller that provides user controls and diagnostic images on a single surface within the field of operation. In alternative embodiments, however, the bedside controller 118 may include both a non-interactive display and separate controls 120 such as physical buttons and/or a joystick, and/or a keyboard and mouse. In the integrated medical system 100, the bedside controller 118 is operable to present control options for the intravascular device 114 and patient imaging data collected therefrom in graphical user interfaces (GUIs).

The medical system 100 provides a medical imaging system interface by which a stent may be observed after deployment of the stent to monitor the success of the deployment, thereby avoiding underdeployment of the stent, and by which an estimate or prediction of a probability of restenosis may be communicated to the clinician. More detail regarding the estimation of a restenosis probability is provided herein.

FIGS. 2A-2F are a series of cross-sectional views that illustrate the insertion and use of therapeutic and imaging catheter(s) into a patient. In some embodiments, the catheter 200 is an integrated catheter, including both imaging and therapeutic capabilities. In other embodiments, separate catheters or devices are utilized for treatment and imaging. In such embodiments, the therapeutic treatment is performed using a first catheter is positioned within the illustrated vessel, and the imaging is performed using a separate catheter having imaging capabilities. Additionally, in some embodiments the catheter 200 may include multiple therapeutic modes. For example, the catheter 200 may be configured to include a balloon assembly for stent deployment, to provide for lesion ablation, and gather images of the site, and may include specialized structures and transducers to provide these and other features.

As illustrated in FIGS. 2A-2F, the catheter 200 includes a balloon assembly 202 and an imaging device 203 being sized and shaped for use within a vessel 210 of the patient 103 of FIG. 1. In some embodiments, the vessel 210 may be an artery. As illustrated, the catheter 200 includes an inner sleeve 204. In some embodiments, the inner sleeve 204 has high pressure capability greater than 20 ATM, which makes the balloon assembly 202 suitable for non-compliant post dilatation. For example, FIGS. 2A-2F illustrate the use of the catheter 200 to access an intravascular lesion 206, assess the intravascular lesion 206, and treat the intravascular lesion 206 using a treatment device, such as an expandable stent 208, according to one embodiment of the present disclosure. The catheter 200 is also used to assess the placement of the expandable stent 208 within the vessel 210. The assessment of the placement of the expandable stent 208 may be performed by collecting imaging data and other data (e.g., pressure, flow, etc.) both before and after the placement of the stent 208. Such data may include information describing a tissue type at the site, a plaque type at the site, a type of the stent, and/or the location of the stent and lesion within the vessel. For example, the tissue type(s) and plaque type(s) at the site may be collected by imaging with the imaging device 203 using a virtual histology approach, such as those described in one or more of U.S. Pat. No. 6,200,268 titled "VASCULAR PLAQUE CHARACTERIZATION," U.S. Pat. No. 6,381,350 titled "INTRAVASCULAR ULTRASONIC ANALYSIS USING ACTIVE CONTOUR METHOD AND SYSTEM," U.S. Pat. No. 7,074,188 titled "SYSTEM AND METHOD OF CHARACTERIZING VASCULAR TISSUE," U.S. Pat. No. 7,175,597 titled "NON-INVASIVE TISSUE CHARACTERIZATION SYSTEM AND METHOD," U.S. Pat. No. 7,215,802 titled "SYSTEM AND METHOD FOR VASCULAR BORDER DETECTION," U.S. Pat. No. 7,359,554 titled "SYSTEM AND METHOD FOR IDENTIFYING A VASCULAR BORDER," and/or U.S. Pat. No. 7,463,759 titled "SYSTEM AND METHOD FOR VASCULAR BORDER DETECTION," each of which is hereby incorporated by reference herein in its entirety.

In the pictured embodiment, the treatment device comprises balloon assembly 202 the expandable stent 208. In other embodiments, the stent 208 may comprise any of a variety of expandable devices shaped and configured to be carried on the balloon assembly 202 or another part of the catheter for the treatment intravascular lesions. Further, the catheter 200 may be configured to deploy other treatments. For example, the treatment device may comprise a scaffolding device, a valve device, a filtering device, a stent graft, an ablation device, a drug delivery or an elution device. In some instances, the treatment device may be designed to indefinitely remain in the vessel after removable of the catheter 200. In other instances, the treatment device may be designed for removal along with the catheter 200 or removal at a later time.

Figure 2A:
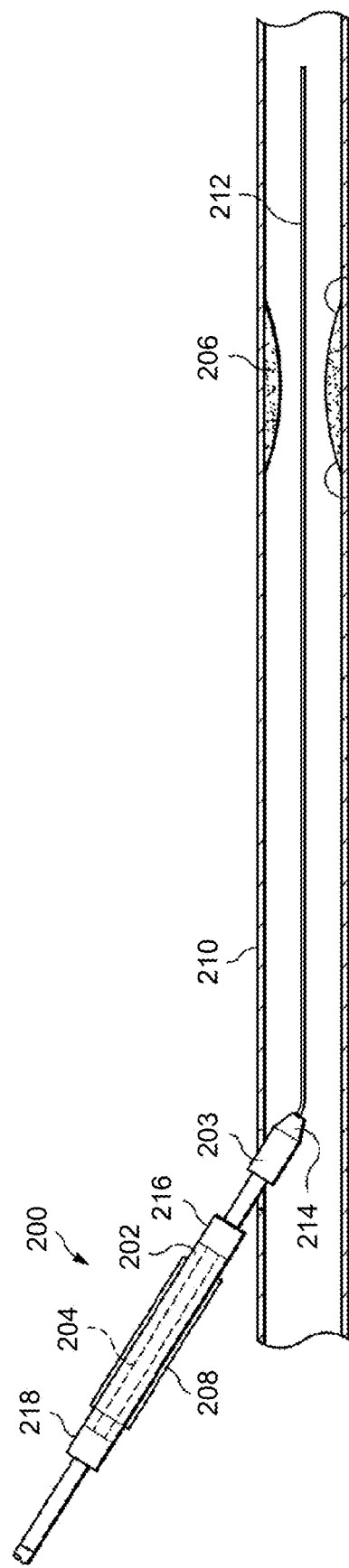

FIG. 2A illustrates the catheter 200 being advanced into a patient's vessel 210. Initially, a guidewire 212 is fed into the vessel 210. In one aspect, a guidewire 212 having a diameter of approximately 0.014 inches can be utilized. The catheter 200 can then be moved along the guide-wire 212 deeper into the patient's vessel 210. During insertion of the catheter 200 into the vessel 210, the balloon assembly 202 is not inflated and maintains a low profile in an unexpanded condition. A distal end 214 of the catheter 200 can be designed to facilitate entry and progress through the vessel 210. For example, the distal end 214 may be tapered.

As shown in FIG. 2A, the catheter 200 is pushed into the vessel 210 until the imaging device 203 and a distal junction 216 of the balloon assembly 202 enters the vessel 210. The catheter 200 is then pushed further into the vessel 210 until a proximal junction 218 of the balloon assembly 202 enters the vessel 210. Thereafter, the catheter 200 is pushed further into the vessel 210, guided along by a guidewire 212, with a proximal shaft 220 of the catheter 200 extending outside the vessel 210 and outside the patient.

Figure 2B:
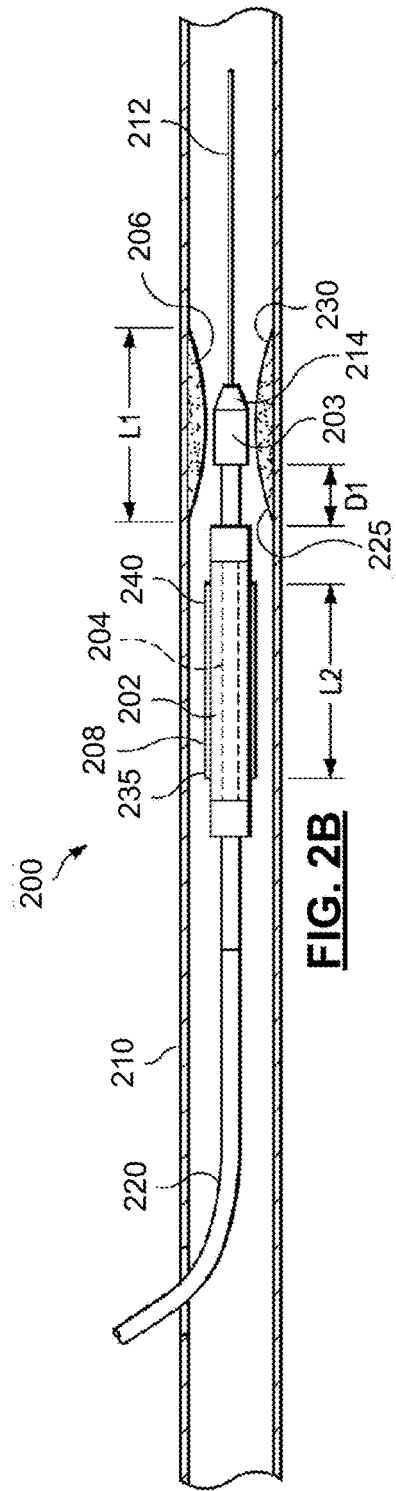

FIG. 2B illustrates the catheter 200 moving through the lesion 206 in the patient's vessel 210. The imaging device 203 can be used to detect and assess the lesion 206 to facilitate placement of the stent 208. The lesion 206 includes a proximal end 225 and a distal end 230 and has a length L1 extending from the proximal end 225 to the distal end 230 of the lesion 206. As the catheter 200 traverses the vessel 210, a clinician can view the data obtained by the imaging device 203 to assess the health of the vessel. The imaging data may also relay other vascular characteristics, such as, by way of non-limiting example, the path and/or tortuosity of the vessel 210, information regarding the location of the lesion 206 within the vessel 210, the regularity or irregularity of the vessel walls within the vessel 210, and various characteristics about the blood flow within the vessel 210. The imaging data may be processed by the processing system 101 of FIG. 1 to identify the types of tissue and/or plaque present at the site of the lesion 206. Upon visualizing the lesion 206, the catheter 200 is advanced further into the vessel 210 until the balloon assembly 202 is aligned with the occlusion 206. The imaging device 203 can continue to image the vessel as the distal end 214 of the catheter 200 travels through the lesion 206, thereby providing the clinician with an accurate assessment of the location of the balloon assembly 202. In particular, the imaging device 203 is positioned a known distance D1 from the balloon assembly 202, which allows a clinician to advance and/or retract the catheter 200 the known distance to position the balloon assembly 202 relative to whatever portion of the vessel 210 the imaging device 203 is imaging at a given time.

Figure 2C:
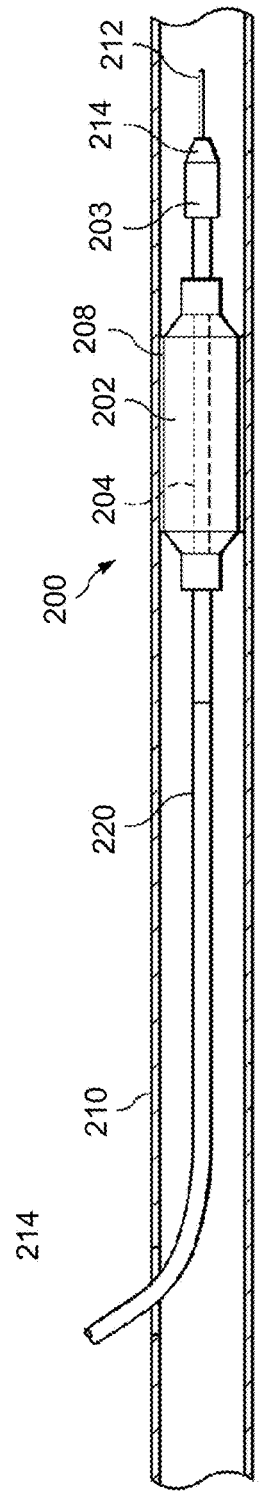

The imaging device 203 can also be used to facilitate placement of the balloon assembly 202 relative to the lesion 206. In the illustrated example, the lesion 206 is an intravascular occlusion that may require reduction and stenting as a treatment option. As shown in FIGS. 2B and 2C, as the imaging device 203 travels through the lesion, the imaging data relayed by the imaging device 203 can provide information of various anatomic characteristics within the vessel 210, such as, by way of non-limiting example, the length L1 of the lesion 206, the luminal contours and cross-sections of the lesion 206 (e.g., the intraluminal diameter of the vessel 210 proximal, adjacent, and distal to the lesion 206), and characteristics of the blood flow through the lesion 206, etc. Using this imaging data, the clinician can advance the catheter 200 an appropriate distance forward to accurately position the unexpanded balloon assembly 202 and overlying stent 208 within the lesion 206. The stent 208 includes a length L2 extending from a proximal stent end 235 to a distal stent end 240. The clinician can assess whether the length L2 of the stent is appropriate to treat the lesion 206, which has the length L1. If the stent 208 is comparatively too short or too long to appropriately treat the lesion 206, the catheter 200 may be removed and a correctly-sized stent may be provided, thereby avoiding the potential stent failure, collapse, ineffective treatment, or less effective treatment that may result from implantation of an inappropriately-sized stent.

FIG. 2C illustrates the expansion of the balloon assembly 202 and the stent 208 within the lesion 206 in the patient's vessel 210. After the clinician advances the balloon assembly 202 and the stent 208 (in an unexpanded condition) appropriately within the lesion 206, the clinician may inflate the balloon assembly 202 by introducing a pressure therein to both compress the plaque or other material causing the lesion 206 and expand the stent 208 to maintain the new patency of the vessel 210 at the location of the lesion 206. As mentioned above, this may be done by pumping an inflation fluid through an inner lumen of the proximal shaft 220 of the catheter 200. As the balloon assembly 202 is inflated under a pressure, typically in the range of 15-25 ATM, the stent 208 assumes an expanded condition and compresses the material of the lesion 206 against inner walls of the vessel 210.

FIG. 2D illustrates the withdrawal of the balloon assembly 202 from the lesion 206 after initial deployment of the stent 208 within the lesion 206. The clinician may deflate the balloon assembly 202 and retract or pull back the catheter 200 until the imaging device 203 is positioned proximal to the stent 208. The clinician or a processing system can access and use imaging data received by the imaging device 203 as it is pulled back through the deployed stent 208. This imaging data may be referred to as pullback imaging data. The imaging data may be used to assess the expansion and deployment of the stent 208. In particular, the imaging data allows the clinician to assess appropriate stent apposition against the lesion 206 and the arterial wall.

The pullback imaging data and other data may be processed by the processing system 101 to estimate a probability of restenosis. The processing system 101 may estimate the restenosis probability based on the deployment of the stent 208 (such as amount of deployment of the stent 208 relative to the diameter of the vessel on either side of the lesion 206), a tissue type or types present at the site of the lesion 206, the type of stent, and the location of the stent 208 within the vessel 210. In some embodiments, the degree of deployment of the stent 208 may be determined as a percentage of the pre-deployment diameter of the vessel 210 at the site of the lesion 206, as a percentage of a target or desired deployment diameter, or as a percentage of a diameter or average diameter of the vessel 210 on either side of the lesion 206, or as a percentage of the cross-sectional areas before and after the deployment of the stent 208.

For example, when the degree of deployment of the stent 208 is indicated from the pullback imaging data as being less than a threshold value, the processing system 101 may determine objectively that there is a high probability of restenosis. This restenosis probability value may be communicated to a clinician in a variety of ways. In some embodiments, a visual indication of the restenosis probability value may be displayed on the bedside controller 118 or the display 122 of FIG. 1. The threshold value may be 60%, 75%, 80%, 95%, or another percentage. While this example estimates the restenosis probability value based on the degree of deployment, in many embodiments, multiple factors are included to estimate or calculate the restenosis probability value.

Occasionally, as shown in FIG. 2D, the expansion of the stent 208 is insufficient to adequately treat the lesion 206. In some procedures, the expansion of the stent 208 may appear to be sufficient to treat the lesion 206 based on angiography imaging or pressure analysis, but is not actually sufficient or is not likely to be maintained in the future. For example, pressure measurements taken proximally and distally to the stent 208 after deployment of the stent 208 may indicate a satisfactory level of improvement in the flow through the vessel 210 at the current time. However, the collected imaging data of the site of the stent 208 may indicate a high probability of restenosis. For example, if a portion of the stent 208 is not positioned against the wall of the vessel 210, this portion may become a favorable site for plaque deposits in the future. Accordingly, even when pressure measurements indicate that the performance of the stent 208 is satisfactory, imaging data obtained by a pullback of the catheter 200 may provide additional information in assessing the performance, both now and in the future, of the stent 208.

In FIG. 2D, the stent 208 has not fully expanded to compress the lesion 206 against luminal walls 245 of the vessel 210. Instead, the lesion 206 remains partially intact and capable of at least partially occluding flow through the vessel 210. The imaging device 203 can convey this information via imaging data to the clinician and the processing system 101 may estimate the restenosis probability value and communicate it visually and/or by audio to the clinician. For example, when the processing system 101 estimates the restenosis probability value of the stent 208, which is not fully expanded as shown in FIG. 2D, is above a threshold value the processing system may cause a beep or chime to be produced on a speaker coupled to the processing system 101. Additionally or alternatively, the processing system 101 may cause a notification to be displayed to the clinician. The notification or alert, such as a visual notification or audio notification, associated with the estimated restenosis probability value may indicate to the clinician that the stent 208 is not positioned satisfactorily and that ameliorative measures should be considered. These ameliorative measures may include performing corrections to the deployment of the stent 208 or performing an alternative procedure, such as an ablation procedure to remove material from the site of the lesion 206. In some embodiments, the processing system 101 may generate a recommended intervention (e.g., a higher pressure deployment of the stent 208, an ablation process, or a combination thereof, etc.) and communicate the recommendation to the clinician in a user interface provided by the processing system 101.

FIG. 2E illustrates the reinsertion and re-expansion of the balloon assembly 202 within the lesion 206 to improve the deployment of the stent 208. The placement of the stent 208 may be assessed again, and if the restenosis probability value is still above a threshold additional steps may be taken. After the estimation of the restenosis probability value, if the clinician desires to increase the expansion of the stent 208 and further decrease the profile of the lesion 206, the clinician may re-advance the catheter 200 and re-position the balloon assembly within the stent 208 and the lesion 206. As shown in FIG. 2E, the balloon assembly 202 may be re-inflated at a higher pressure to further expand the stent 208, thereby improving the stent apposition and/or expansion against the luminal walls 245 of the vessel 210.

FIG. 2F illustrates the withdrawal of the balloon assembly 202 from the lesion 206 after the secondary expansion of the stent 208 within the lesion 206. The clinician may once again deflate the balloon assembly 202 and retract the catheter 200 until the imaging device 203 is positioned proximal to the stent 208. The processing system 101 may again use the imaging data obtained by the imaging device 203 during the pullback to assess the expansion and deployment of the stent 208 to estimate another restenosis probability value based on the new conditions. The estimated restenosis probability value may provide an indication to the clinician that there is appropriate stent apposition against the lesion 206 and expansion within the vessel 210 and that the future performance of the stent 208 is likely to continue without restenosis. If the estimated restenosis probability is below a threshold value, the processing system 101 may indicate the appropriate deployment of the stent 208 (i.e., appropriate positioning, expansion, and apposition) to the clinician. Then, the clinician may withdraw the catheter 200 from the vessel 210 (and the patient's body). In some embodiments, the processing system 101 may indicate that the deployment of the stent 208 is satisfactory. Similarly, the processing system 101 may simply not provide an indication that the deployment of the stent 208 is unsatisfactory.

Figure 3:
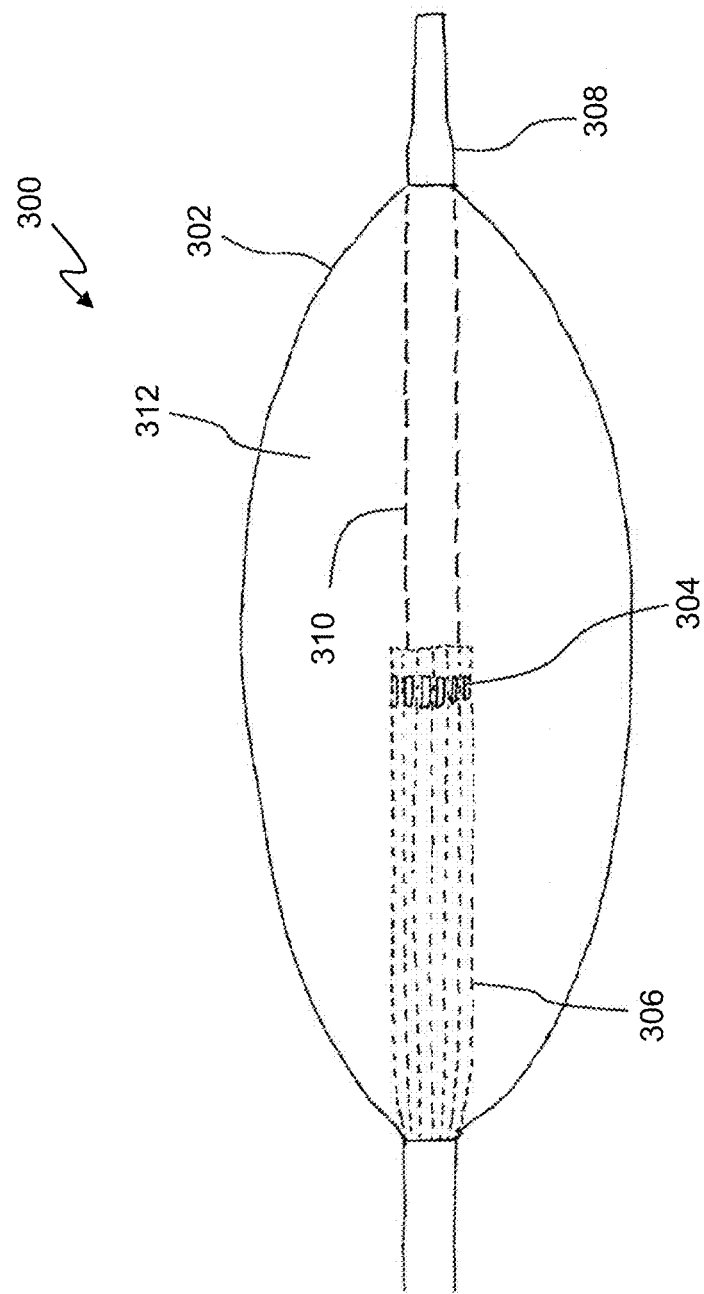
FIG. 3 is a diagrammatic, partially cross-sectional view of an imaging catheter device, according to some embodiments of the present disclosure.

FIG. 3 illustrates a device 300 including an imaging catheter for imaging a vessel via intravascular ultrasound (IVUS) while using a balloon 302. The imaging catheter device 300 may be used as described above in connection with the catheter 200 in FIGS. 2A-F. The imaging catheter device 300 includes an imaging assembly 304 configured within the balloon 302. Preferably, imaging assembly 304 includes any technology suitable for intravascular imaging such as technologies based on sound, light, or other media. The catheter 300 may include an imaging portion 306 (e.g., with conductor wires extending therethrough, surrounding an inflation lumen, guidewire lumen, or both, and extends to distal tip 308.

As mentioned previously, in some embodiments, the imaging assembly 304 is an IVUS imaging assembly. The imaging assembly can be a phased array IVUS imaging assembly or a rotational IVUS imaging assembly. In some embodiments, an IVUS array is configured to image beyond the distal end of the catheter, i.e., forward-looking IVUS. In other embodiments, the imaging assembly 304 may use optical coherence tomography (OCT). OCT is a medical imaging methodology using a miniaturized near infrared light-emitting probe, and is capable of acquiring micrometer-resolution, three-dimensional images from within optical scattering media (e.g., biological tissue).

The imaging catheter device 300 includes a catheter 310 with an extended body terminating at a distal tip 308. The catheter 310 may have one or more lumens therein such as, for example, a guidewire lumen to allow the catheter 310 of the device 300 to be guided to a treatment site. The catheter 310 may include a separate inflation lumen allowing fluid 312 (e.g., air) to be delivered to, and to inflate, balloon 302. The catheter 310 may also include the imaging device 304. In FIG. 3, the imaging device 304 is depicted as being located within balloon 302. A portion 306 of catheter 310 carries requisite hardware for imaging assembly 304 such as conductors or optical fibers. Imaging assembly 304 may operate via any suitable imaging modality including, for example, ultrasound, opto-acoustic imaging, OCT, or others. The imaging catheter device 300 may be used as generally described above in connection with FIGS. 2A-F. However, the imaging catheter device 300 may be used to obtain at least some imaging data while the balloon 302 is being deployed to place a stent at the site of a lesion.

Figure 4:
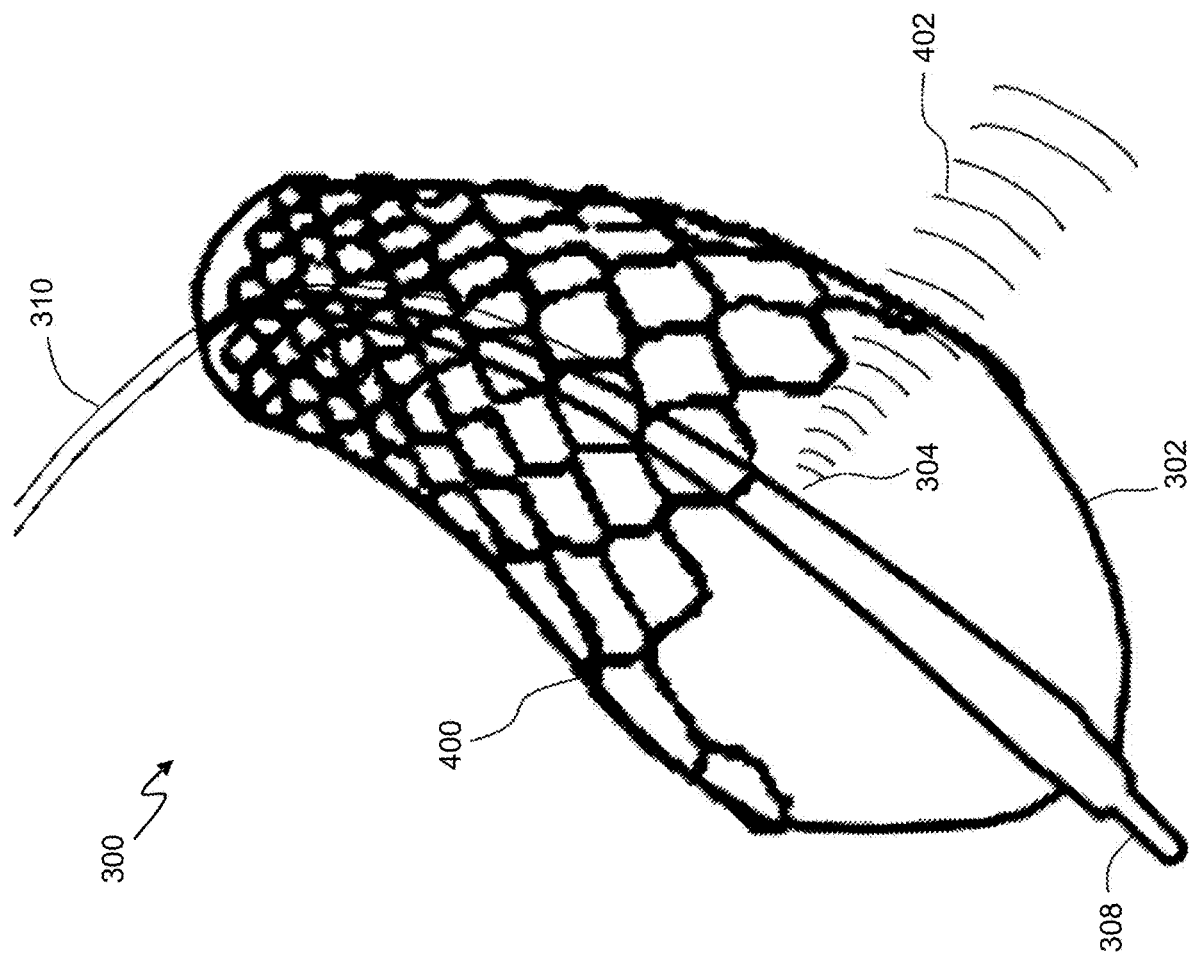
FIG. 4 is a perspective view of the imaging catheter device of FIG. 3 showing the stent thereon, according to embodiments of the present disclosure.

FIG. 4 illustrates the imaging catheter device 300 of FIG. 3 with a stent 400 being deployed by the expansion of the balloon 302. As shown in FIG. 4, imaging data is collected based on the reflected signals produced by sound waves 402 emitted from the imaging assembly 304 while the balloon 302 is expanding to place the stent 400. Accordingly, in some embodiments, collecting imaging data from the site of a lesion may be performed before, after, and during deployment of a stent or other treatment. This imaging data may be processed by the processing system 101 to identify tissues and plaque at the site and to characterize the site and/or lesion in terms of physical dimensions. Further, the processing system 101 may estimate a restenosis probability during placement of the stent 400. The processing system 101 may provide an indication of the restenosis probability value to a clinician during placement of the stent 400. In some embodiments, the restenosis probability value calculated during deployment of the stent 400 may be communicated as being a preliminary restenosis value. In some embodiments, the restenosis probability value may be estimated repeatedly during deployment of the stent 400, such that when the restenosis probability value falls below a threshold value, an indication is provided to a clinician through a user interface to indicate that the probability of restenosis is acceptably small.

Figure 5:
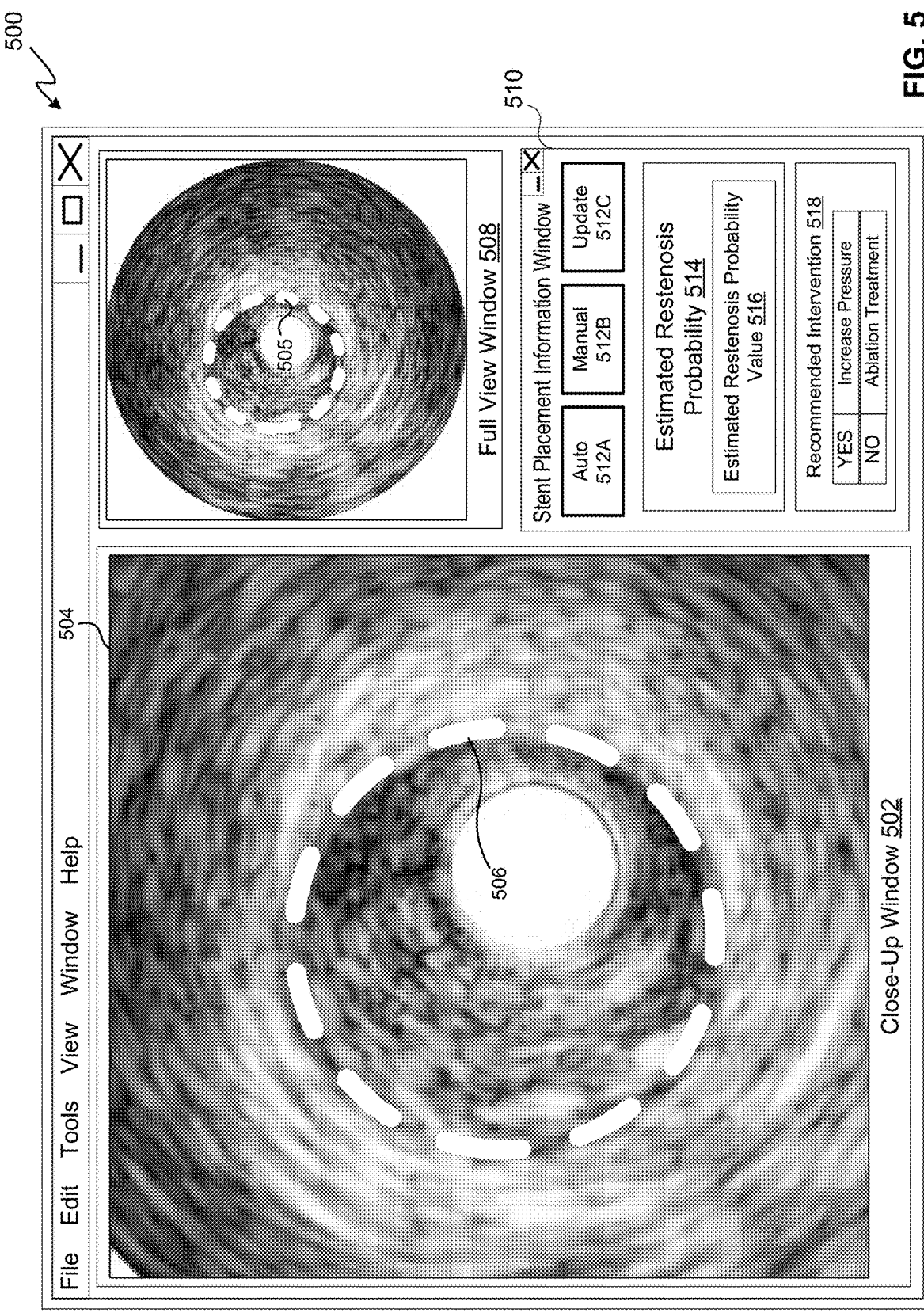
FIG. 5 is a visual depiction of a user interface provided by a medical system, according to some embodiments of the present disclosure.

FIG. 5 depicts a user interface 500, according to an embodiment of the present disclosure, that may be provided by the processing system 101 for display by the bedside controller 118 and/or the display 122 of FIG. 1. The user interface 500 may also be referred to as a screen display. The user interface 500 may include multiple tabs or be accessible as a tab within an overall user interface associated with the processing system 101 and or the intravascular device 114 of the medical system 100 illustrated in FIG. 1. The user interface 500 may include a close-up window 502 that displays a portion of the imaging data 504 obtained from a site of a stent placement. When rendered in the close-up window 502 in a display, the imaging data 504 includes a depiction of the stent 506 within the vessel. The stent 506 is at least partially deployed. The displayed portion of imaging data 504 may show the stent 506 in a nearly cross-sectional view. The close-up window 502 may enable a clinician to visualize the placement of a stent, such as the stent 208 or 400 of FIGS. 2A-F and 4, respectively. The clinician may also be able to see the cross-sectional configuration of the vessel at the site of the stent 506. Vessels may deviate from a generally circular cross-section to varying degrees that may not be observed externally, but may be observed using intravascular imaging devices.

The user interface 500 may also include a full view window 508 that may display the full current view of the rendered imaging data 504. In some embodiments, the windows 502 and 508 may include "live" imaging data. In other embodiments, one or both of the windows 502 and 508 may display non-live or recorded imaging data. In some embodiments, different modes of images may be displayed in the windows 502 and 508. For example, imaging data obtained in a manner to optimize the depiction of plaque may be shown in the window 502, while imaging data obtained in manner to optimize the depiction of tissue may be shown in the window 508. The imaging data may be obtained by alternating between imaging modes. The imaging modes may be provided by processing a single set of imaging data in different ways or the modes may be provided by alternating between settings and parameters implemented by the imaging device within the catheter to best capture certain features at the imaging site. For example, the imaging techniques described in U.S. Provisional Patent Application No. 61/903,764, filed Nov. 13, 2013 and titled "Visually Optimized Intravascular Imaging and Associated Devices, Systems, and Methods," which is hereby incorporated by reference in its entirety, may be utilized. Using the visuals provided by the user interface 500, a clinician may apply subjective judgment, based on experience, to assess the quality of the placement of the stent.

The user interface 500 further includes a stent placement information window 510. The stent window 510 may be used to communicate objective information regarding the placement of a stent within a patient's vessel. The information recording the placement of the stent is based on physiological measurements taken by sensors within the vessel, such as intravascular imaging data. The clinician may interact with the user interface 500 to enable or disable the estimation of the probability of restenosis. As shown in FIG. 5, the window 510 include an auto button 512A by which the user of the user interface 500, e.g., a clinician, may affirmatively request that an estimated restenosis probability value is automatically and continuously calculated by the processing system 101 as physiological data becomes available. The physiological data may become available by being collected using a catheter, such as an IVUS imaging catheter, and/or by being accessed from a memory, such as a networked storage device having physiological data stored thereon. The manual button 512B may be selected to limit the estimation process. Upon selecting the manual button 512B, a manual mode is activated, in which an estimated restenosis probability value is calculated when the update button 512C is selected by the clinician. Buttons 512A-C may be selected by clicking a mouse, entering an associated keystroke on a keyboard, and/or by touching a touch-screen.

The stent placement information window 510 includes an estimated restenosis probability area 514 that may display an indication of a most current estimated restenosis probability value 516. The estimated restenosis probability value 516 may be communicated through the user interface 500 in a variety of ways, only some of which are described herein. For example, the restenosis probability value 516 may be provided as a numerical value. In other embodiments, a qualitative description of the quantitative, estimated restenosis probability value 516 may be provided by applying a plurality of value brackets. For example, when the estimated restenosis probability value is between a first bracket-defining value and a second bracket-defining value, a qualitative description of that bracket may be provided in the estimated restenosis probability value area 514, such as "poor," "fair," "good," or "excellent." In this way, the processing system 101 may communicate qualitative descriptions of the estimated restenosis probability value that may be more easily interpreted by the clinician than the actual estimated restenosis probability value itself. In some embodiments, a color may be displayed to indicate the bracket in which a most recent estimated restenosis probability value belongs, e.g., "red," "yellow," or "green." In other embodiments, the user interface 500 may include audio cues to indicate an estimated restenosis probability value. For example, the user interface 500 may cause an alert or a beep to be generated through a speaker whenever the most recent estimated restenosis probability value is above a threshold value. Regardless of the manner in which the estimated restenosis probability value 516 is communicated to a user of the user interface 500, the estimated restenosis probability value 516 may communicate that the current placement of a stent may not be providing adequate compensation for a lesion and/or may not provide adequate compensation for the lesion in the future. The estimated restenosis probability value 516 may indicate that, although flow through the stent is improved after initial placement, the benefits of the stent may not last unless additional steps are taken.

The stent placement information window 516 also includes a recommended intervention area 518, in some embodiments. In embodiments in which a particular intervention may be determined by the processing system 101 to best improve the performance of a stent, the determined means of achieving that improvement may be displayed for communication in the user interface 500. As shown in FIG. 5, the processing system 101 has determined that the estimated restenosis probability value is above a threshold value and that redeploying the stent by re-expanding a balloon at a distal portion of the catheter using an increased pressure may improve the performance of the stent in the future. As illustrated in user interface 500, the processing system 101 indicates that an ablation treatment is not recommended. In some embodiments more than one intervention may be displayed to a user with accompanying indications of whether the intervention is likely to improve the performance of the stent in the future. In other embodiments, a single recommended intervention may be displayed in the recommended intervention area 518. The user interface 500 may include further buttons or user interface elements to enable a clinician to program threshold values that may be used with the estimated restenosis probability value to customize the indications of stent placement performance.

Referring now to FIG. 6, illustrated therein is a flowchart of a method 600 of treating a vessel within a patient. For example, the method 600 illustrates a method for treating a vessel of the patient 103 of FIG. 1 using the medical system 100. The method 600 is illustrated as a plurality of enumerated steps or operations. Embodiments of the method 600 may include additional steps or operations before, after, in between, or as part of the enumerated steps. The steps of the method 600 may be performed using hardware such as the intravascular device 114, the processing system 101 including the CPU 104, and the display 122 or display of the bedside controller 118. In some embodiments, the instructions for performing some or all of the operations of the method 600 may be stored as executable code on a non-transitory computer readable medium such as the memory 106 of FIG. 1.

The steps of method 600 in FIG. 6: a catheter is inserted into a lumen of the vessel (step 601); collect intravascular ultrasound imaging data of the placement of the stent at the site of the lesion using the intravascular ultrasound imaging device disposed on the catheter (step 602); estimate, using a processing device, a restenosis probability value based on the intravascular ultrasound imaging data of the placement of the stent at the site of the lesion (step 604); communicate an indication of the estimated restenosis probability value to a clinician (step 606).

As illustrated in FIG. 6, embodiments of the method 600 may include step 604, in which a processing device such as the CPU 104 of the processing system 101 estimates a restenosis probability value based on the intravascular ultra sound imaging data of the placement of the stent at the site of the lesion. Many algorithms may be used to process the collected imaging data obtained at the site of the lesion and other information to generate an objective measure of restenosis probability. The processing device may estimate the restenosis probability value based on tissue types at the site, plaque types at the site and/or plaque presence and geometry, a type of the stent, and/or the location of the stent within the vessel, the presence of gaps between the stent and the walls of the vessel, the cross-sectional area through the stent (including the shape and/or size of the area and the uniformity of the cross-sectional area through the stent), whether the lesion extends beyond the stent, etc. In some embodiments, the processing device may estimate the restenosis probability value based on the degree of curvature in the vessel in areas proximal to the stent. Additionally, in some embodiments in which data other than imaging data is used to provide information regarding the performance of the stent, the estimation of the restenosis probability value may be based on physiology measurements such as pressure data and/or flow data. For example, pressure information may be obtained at locations before and after the stent and at various points within the stent. This pressure information may be used to assess the performance of the stent and may be used in estimates of the restenosis probability value. In some embodiments, pressure information may be used by the processing device along with the imaging data to generate the estimated restenosis probability value.

At step 601, a catheter is inserted into a lumen of the vessel. This may be done as shown in FIGS. 2A and 2B as described herein. The catheter may include a stent placement assembly, like the balloon assembly 202 of FIGS. 2A-F or the balloon 302 shown in FIGS. 3 and 4 as described herein, and an intravascular ultrasound imaging device. Such as the imaging assembly 304, also of FIGS. 3 and 4. In some embodiments of the method 600, the catheter may be inserted by manual control of the catheter by a clinician, the catheter may be inserted using robotic control at the direction of the clinician, or the catheter may be inserted using automatic robotic control wherein the catheter is steered by the processing system 101 to the site of the lesion. For example, the catheter may be a steerable intravascular device 114, coupled to a PIM 116 that received commands from the processing system 101, or directly from the bedside control 118, to steer the catheter's tip and direct the catheter into and out of a vessel. After the catheter is positioned at the site of a lesion within the lumen of the vessel, the stent placement assembly may be activated to place the stent at the site of the lesion within the lumen of the vessel, as depicted in FIG. 2C. In placing a stent, the stent may be deployed such that it expands against the walls of the lumen to improve flow within the vessel.

At step 602, intravascular ultrasound imaging data is collected using the intravascular ultrasound imaging device of the catheter. This may be done while performing a pullback of the catheter, such that imaging data is obtained along the vessel from a distal side of the stent or the lesion and to a proximal side of the stent or the lesion. The imaging data includes information about the placement of the stent at the site of the lesion and may be processed by the processing system 101 to provide specific information regarding tissue types, plaque presence and/or types, and information regarding the location of the stent within the vessel (e.g., whether the vessel include pronounced bends, the stent diameters on either side of the stent, etc.). For example, the information may include information regarding the cross-sectional area of the vessel before and after the stent and within the stent. Thus, when the stent is not deployed having a generally circular cross-sectional area, the intravascular ultrasound imaging device may provide information to indicate this to the clinician. Additionally, if gaps are present between the stent and the luminal walls in some portion of the span of the stent, the imaging data may include information enabling the processing system 101 to interpret and analyze the gap and provide visualization of the gap in a display in some embodiments.

At step 604, a processing device such as the CPU 104 of the processing system 101 may estimate a restenosis probability value based on the intravascular ultrasound imaging data of the placement of the stent at the site of the lesion. Many algorithms may be used to process the collected imaging data obtained at the site of the lesion and other information to generate an objective measure of restenosis probability. The processing device may estimate the restenosis probability value based on tissue types at the site, plaque types at the site and/or plaque presence and geometry, a type of the stent, and/or the location of the stent within the vessel, the presence of gaps between the stent and the walls of the vessel, the cross-sectional area through the stent (including the shape and/or size of the area and the uniformity of the cross-sectional area through the stent), whether the lesion extends beyond the stent, etc. In some embodiments, the processing device may estimate the restenosis probability value based on the degree of curvature in the vessel in areas proximal to the stent. Additionally, in some embodiments the data other than imaging data may be used to provide information regarding the performance of the stent. For example, pressure information and/or flow information may be obtained at locations before and after the stent and at various points within the stent. This pressure and flow information may be used to assess the performance of the stent and may be used in estimates of the restenosis probability value. In some embodiments, pressure information may be used by the processing device along with the imaging data to generate the estimated restenosis probability value.

At step 606, an indication of the estimated restenosis probability value is communicated to a clinician. For example, the processing system 101 may cause an indication of the estimated restenosis probability value to be displayed in the display 122 or in a touchscreen display of the bedside controller 118. For example, the processing system 101 may cause a user interface, such as the user interface 500 to be displayed. As shown in FIG. 5, the user interface 500 includes a stent placement information window 510 as described herein. The estimated restenosis probability value 516 may be displayed in the estimated restenosis probability area 514 is a numerical value, is a color, as text, or as a combination thereof. In some embodiments the estimated restenosis probability value may be interpreted by the processing system 101 before display to the clinician. For example, the estimated restenosis probability value may be compared with a plurality of brackets that map to descriptions of estimated restenosis probability, such as "poor," "fair," "good, etc. In some embodiments, the indication of the estimated restenosis probability value may be communicated to the clinician is a sound, such as a beep, a chime, or an alarm to indicate that restenosis is likely or unlikely as indicated by the imaging data and other information obtained by the catheter at the site of the lesion after placement of the stent. Based on the estimated restenosis probability, the clinician may reinsert the stent deployment assembly within the stent and apply pressure again to deploy the stent, as shown in FIGS. 2E and 2F. Thereafter, data may be collected, and the restenosis probability may be calculated again to predict future stent performance in view of the redeployment.

Referring now to FIG. 7, shown therein is a flow chart of a method 700 of treating a vessel within a patient. Like the method 600 of FIG. 6, the method 700 is illustrated as a plurality of steps or operations. Additional steps may be performed before, after, in between, or as part of these enumerated steps. Steps of the method 700 may be performed by the medical system 100 of FIG. 1. An embodiment of the method 700 may begin at step 702 in which a catheter is positioned at a site of a lesion within a lumen of the vessel. The catheter includes a stent placement assembly. At step 704, the stent placement assembly is activated place the stent at the site of the lesion within the lumen of the vessel. For example, as shown in FIG. 3, the catheter may include a balloon 302 that may be deployed and the fluidic pressure to cause the stent to expand against the luminal walls of the vessel. For example, the stent may be deployed as illustrated in FIG. 4 by the stent 400. Once deployed, the stent may restore flow through the vessel.

In order to assess whether the stent is likely to provide long-term, future benefits, a restenosis probability value is estimated based on the placement of the stent at the site of the lesion, at step 706. The restenosis probability value may be estimated by the processing system 101 of FIG. 1. For example, the CPU 104 may receive imaging data and/or other data obtained within the vessel at the placement of the stent and may analyze the data to determine tissue types, plaque types, the location of the stent within the vessel including the cross-section of the vessel at multiple points within the stent and the degree of bending of the vessel or adjoining vessels near the stent. Additionally, the CPU 104 may receive imaging data and/or other data obtained prior to the placement of the stent. The CPU 104 may execute algorithms and methods stored as executable code in the instructions 112 on the memory 106. In some embodiments of the method 700, an indication of the estimated restenosis probability value may be communicated to a clinician to inform the clinician that an intervention should be performed so that long-term future benefits of the stent may be achieved. For example, the processing system 101 may determine that the estimated restenosis probability value would be increased by inserting the balloon 302 into the stent again and re-inflating the balloon using a higher pressure than originally employed. The processing system 101 may determine that the estimated restenosis probability value would be increased by inserting an ablation device within the stent and performing an ablation process to remove some of the plaque from the site of the lesion. The stent may be redeployed using a higher pressure or using the same pressure after the ablation process. Upon termination of each intervention, data may be obtained at the placement of the stent to assess and re-assess the restenosis probability by an estimation algorithm. For example, the processing system 101 may determine from the imaging data that a stent is deployed, in at least some portion of the stent, to only a fraction, such as 65%, of its maximum diameter. Other algorithms may include different threshold values and may operate on more variables extracted from the imaging data.

Referring now to FIG. 8, shown therein is a flow chart of a method 800 of treating a vessel of the patient. As illustrated, the method 800 includes a step 802 in which imaging data is received. The imaging data is obtained by, and received from, an imaging device on a catheter at a placement site of a stent within a lumen of a vessel of a patient. For example, the processing system 101 of FIG. 1 may receive imaging data obtained by the intravascular device 114. The imaging data may have undergone some processing by the PIM 116 and/or the acquisition card 108 prior to reception by the CPU 104 of the processing system 101. In step 804, the processing system estimates the restenosis probability value based on the imaging data obtained by the imaging device. The estimated restenosis probability value may be based on the placement of the stent at the site of a lesion.

At step 806, an indication of the estimated restenosis probability value may be communicated to a clinician. The indication may be communicated in many different ways as described herein. The processing system 101 may send information to a display to communicate the estimated restenosis probability value. Thus, a numerical representation of the estimated restenosis probability value may be displayed on a display coupled to the processing system 101, a sound may be emitted from the speaker of the processing system 101, etc. Additionally, in some embodiments of the method 800, and intervention recommendation may be determined and provided to a clinician when the stent is determined to be under deployed, or otherwise performing unsatisfactorily, based on the imaging data obtained by the imaging device. In some embodiments, the processing system may receive non-imaging data, such as pressure data or other physiological data, obtained by another sensor or sensors included in the catheter. The estimated restenosis probability value may be calculated based on the non-imaging data or on a combination of imaging data and non-imaging data.

In some embodiments, instructions for performing the operations included in embodiments of the method 800 may be stored in a non-transitory computer readable medium, such as the memory 106 of the processing system 101. Accordingly, embodiments of the present disclosure include systems having processing devices, such as the CPU 104 or the processing system 101 more generally, that perform one or more of the methods 600, 700 and 800 when instructions corresponding to one or more of the enumerated steps of these methods are provided as executable code stored on the non-transitory computer readable medium.

At step 606, a processing device such as the CPU 104 of the processing system 101 may estimate a restenosis probability value based on the intravascular ultrasound imaging data of the placement of the stent at the site of the lesion. Many algorithms may be used to process the collected imaging data obtained at the site of the lesion and other information to generate an objective measure of restenosis probability. The processing device may estimate the restenosis probability value based on tissue types at the site, plaque types at the site and/or plaque presence and geometry, a type of the stent, and/or the location of the stent within the vessel, the presence of gaps between the stent and the walls of the vessel, the cross-sectional area through the stent (including the shape and/or size of the area and the uniformity of the cross-sectional area through the stent), whether the lesion extends beyond the stent, etc. In some embodiments, the processing device may estimate the restenosis probability value based on the degree of curvature in the vessel in areas proximal to the stent. Additionally, in some embodiments the data other than imaging data may be used to provide information regarding the performance of the stent. For example, pressure information and/or flow information may be obtained at locations before and after the stent and at various points within the stent. This pressure and flow information may be used to assess the performance of the stent and may be used in estimates of the restenosis probability value. In some embodiments, pressure information may be used by the processing device along with the imaging data to generate the estimated restenosis probability value.

At step 612, an indication of the estimated restenosis probability value is communicated to a clinician. For example, the processing system 101 may cause an indication of the estimated restenosis probability value to be displayed in the display 122 or in a touchscreen display of the bedside controller 118. For example, the processing system 101 may cause a user interface, such as the user interface 500 to be displayed. As shown in FIG. 5, the user interface 500 includes a stent placement information window 510 as described herein. The estimated restenosis probability value 516 may be displayed in the estimated restenosis probability area 514 is a numerical value, is a color, as text, or as a combination thereof. In some embodiments the estimated restenosis probability value may be interpreted by the processing system 101 before display to the clinician. For example, the estimated restenosis probability value may be compared with a plurality of brackets that map to descriptions of estimated restenosis probability, such as "poor," "fair," "good," etc. In some embodiments, the indication of the estimated restenosis probability value may be communicated to the clinician is a sound, such as a beep, a chime, or an alarm to indicate that restenosis is likely or unlikely as indicated by the imaging data and other information obtained by the catheter at the site of the lesion after placement of the stent. Based on the estimated restenosis probability, the clinician may reinsert the stent deployment assembly within the stent and apply pressure again to deploy the stent, as shown in FIGS. 2E and 2F. Thereafter, data may be collected and the restenosis probability may be calculated again to predict future stent performance in view of the redeployment.

Referring now to FIG. 8, shown therein is a flowchart of a method 800 of treating a vessel within a patient. Like the method 600 of FIG. 6, the method 800 is illustrated as a plurality of steps or operations. Additional steps may be performed before, after, in between, or as part of these enumerated steps. Steps of the method 800 may be performed by the medical system 100 of FIG. 1. An embodiment of the method 800 may begin at step 802 in which a catheter is positioned at a site of a lesion within a lumen of the vessel. The catheter includes a stent placement assembly. At step 804, the stent placement assembly is activated place the stent at the site of the lesion within the lumen of the vessel. For example, as shown in FIG. 3, the catheter may include a balloon 302 that may be deployed and the fluidic pressure to cause the stent to expand against the luminal walls of the vessel. For example, the stent may be deployed as illustrated in FIG. 4 by the stent 400. Once deployed, the stent may restore flow through the vessel.

In order to assess whether the stent is likely to provide long-term, future benefits, a restenosis probability value is estimated based on the placement of the stent at the site of the lesion, at step 806. The restenosis probability value may be estimated by the processing system 101 of FIG. 1. For example, the CPU 104 may receive imaging data and/or other data obtained within the vessel at the placement of the stent and may analyze the data to determine tissue types, plaque types, the location of the stent within the vessel including the cross-section of the vessel at multiple points within the stent and the degree of bending of the vessel or adjoining vessels near the stent. Additionally, the CPU 104 may receive imaging data and/or other data obtained prior to the placement of the stent. The CPU 104 may execute algorithms and methods stored as executable code in the instructions 112 on the memory 106. In some embodiments of the method 800, an indication of the estimated restenosis probability value may be communicated to a clinician to inform the clinician that an intervention should be performed so that long-term future benefits of the stent may be achieved. For example, the processing system 101 may determine that the estimated restenosis probability value would be increased by inserting the balloon 302 into the stent again and re-inflating the balloon using a higher pressure than originally employed. The processing system 101 may determine that the estimated restenosis probability value would be increased by inserting an ablation device within the stent and performing an ablation process to remove some of the plaque from the site of the lesion. The stent may be redeployed using a higher pressure or using the same pressure after the ablation process. Upon termination of each intervention, data may be obtained at the placement of the stent to assess and re-assess the restenosis probability by an estimation algorithm. For example, the processing system 101 may determine from the imaging data that a stent is deployed, in at least some portion of the stent, to only a fraction, such as 65%, of its maximum diameter. Other algorithms may include different threshold values and may operate on more variables extracted from the imaging data.

Referring now to FIG. 9, shown therein is a flowchart of a method 900 of treating a vessel of the patient. As illustrated, the method 900 includes a step 902 in which imaging data is received. The imaging data is obtained by, and received from, an imaging device on a catheter at a placement site of a stent within a lumen of a vessel of a patient. For example, the processing system 101 of FIG. 1 may receive imaging data obtained by the intravascular device 114. The imaging data may have undergone some processing by the PIM 116 and/or the acquisition card 108 prior to reception by the CPU 104 of the processing system 101. In step 904, the processing system estimates the restenosis probability value based on the imaging data obtained by the imaging device. The estimated restenosis probability value may be based on the placement of the stent at the site of a lesion.

At step 906, an indication of the estimated restenosis probability value may be communicated to a clinician. The indication may be communicated in many different ways as described herein. The processing system 101 may send information to a display to communicate the estimated restenosis probability value. Thus, a numerical representation of the estimated restenosis probability value may be displayed on a display coupled to the processing system 101, a sound may be emitted from the speaker of the processing system 101, etc. Additionally, in some embodiments of the method 900, and intervention recommendation may be determined and provided to a clinician when the stent is determined to be underdeployed, or otherwise performing unsatisfactorily, based on the imaging data obtained by the imaging device. In some embodiments, the processing system may receive non-imaging data, such as pressure data or other physiological data, obtained by another sensor or sensors included in the catheter. The estimated restenosis probability value may be calculated based on the non-imaging data or on a combination of imaging data and non-imaging data.

In some embodiments, instructions for performing the operations included in embodiments of the method 900 may be stored in a non-transitory computer readable medium, such as the memory 106 of the processing system 101. Accordingly, embodiments of the present disclosure include systems having processing devices, such as the CPU 104 or the processing system 101 more generally, that perform one or more of the methods 600, 800, and 900 when instructions corresponding to one or more of the enumerated steps of these methods are provided as executable code stored on the non-transitory computer readable medium.

Embodiments of the present disclosure provide for the assessment of stents after deployment within a vessel. By using data obtained within the vessel, including data obtained within the stent itself, a probability of restenosis may be estimated based on objective information obtained from the data. Using the objective information, such as imaging data, the processing system may provide an objective indication of current and/or future stent performance. Additionally, the processing system may recommend one or more interventions to improve the current and/or future performance of the stent. By assessing and improving the placement of the stent at the time of placement, one or more future interventions may be avoided. Avoiding unnecessary interventions is beneficial to both patients and clinicians.

What is claimed is:

1. A method of treating a vessel within a patient, the method comprising:
   positioning a catheter at a site of a lesion within a lumen of the vessel, the catheter comprising a stent placement assembly;
   providing treatment of the vessel by activating the stent placement assembly to place the stent at the site of the lesion within the lumen of the vessel;
   determining, using a processing device in communication with an intravascular ultrasound (IVUS) imaging transducer positioned within the vessel, whether there is a probability of restenosis, wherein determining whether there is the probability of restenosis comprises:
   controlling the IVUS imaging transducer to emit ultrasound waves and receive echoes associated with the ultrasound waves;
   obtaining IVUS imaging data of the stent at the site of the lesion based on the received echoes;
   processing the IVUS imaging data to compute a diameter of the vessel and a deployed size of the stent; and
   comparing the computed deployed size of the stent to the computed diameter of the vessel; and
   communicating, via a display coupled to the processing device, a notification indicating that there is the probability of restenosis to a clinician in response to determining that there is the probability of restenosis.

2. The method of claim 1, wherein obtaining the IVUS imaging data comprises using the IVUS imaging transducer to obtain the IVUS imaging data as the IVUS imaging transducer is pulled back through the vessel.

3. The method of claim 2, wherein the IVUS imaging data comprises tissue information.

4. The method of claim 1, wherein determining whether there is the probability of restenosis further comprises determining at least one of:
   a tissue type at the site;
   plaque presence at the site;
   a type of the stent;
   the site of the stent within the vessel; or
   a performance of the stent, wherein the performance is based on at least one of:
   pressure measurements; or
   flow measurements.

5. The method of claim 1, further comprising wherein comparing the computed deployed size of the stent to the computed diameter of the vessel comprises computing a relative deployed size of the stent, and wherein determining whether there is the probability of restenosis comprises determining whether the relative deployed size of the stent exceeds a threshold value.

6. The method of claim 5, wherein the notification comprises at least one of a visual notification or an audio notification.

7. The method of claim 1, wherein determining whether there is the probability of restenosis comprises detecting underdeployment of the stent at the site of the lesion.

8. The method of claim 7, further comprising providing, via the display, a recommendation, to the clinician, to address the underdeployment of the stent at the site of the lesion by redeploying the stent.

9. The method of claim 7, further comprising providing, via the display, a recommendation, to the clinician, to address the underdeployment of the stent by an ablation process.

10. The method of claim 1, wherein processing the IVUS imaging data to compute the deployed size of the stent comprises computing a cross-sectional area of the stent, and wherein determining whether there is the probability of restenosis comprises determining whether there is the probability of restenosis based on the cross-sectional area of the stent.

11. A medical diagnosis and treatment system, comprising:
   a non-transitory computer-readable medium to store instructions thereon; and
   a processing device in communication with the medium and an intravascular ultrasound (IVUS) imaging catheter, wherein the processing device is configured to execute the instructions to perform operations comprising:

receiving IVUS imaging data obtained by the IVUS imaging catheter at a placement site of a stent within a lumen of a vessel of a patient, the placement site corresponding to a location of a lesion of the vessel;

computing a diameter of the vessel and a deployed size of the stent based on the received IVUS imaging data of the stent within the lumen of the vessel;

comparing the computed deployed size of the stent to the computed diameter of the vessel; and determining whether there is a probability of restenosis based on the comparison of the deployed size of the stent to the computed diameter of the vessel; and sending, to a display coupled to the processing device, information communicating whether there is the probability of restenosis to an operator of the medical diagnosis and treatment system.

12. The medical diagnosis and treatment system of claim 11, further comprising the display.

13. The medical diagnosis and treatment system of claim 11, wherein the operations further comprise:
determining whether the stent is underdeployed; and
sending, to the display, an intervention recommendation when the stent is determined to be underdeployed.

14. The medical diagnosis and treatment system of claim 11, wherein determining whether there is the probability of restenosis further comprises receiving non-imaging data obtained by a non-imaging sensor of the catheter, the non-imaging data representative of at least one of pressure or flow of blood within the vessel.

15. The system of claim 11, wherein the information communicating whether there is the probability of restenosis comprises at least one of a quantitative description or a qualitative description.

16. The system of claim 11,
wherein the processing device is configured to perform the operation comprising computing the deployed size of the stent by computing a diameter of the stent,
wherein the diameter of the vessel comprises at least one of the diameter adjacent to the lesion, the diameter proximal to the lesion, or the diameter distal to the lesion; or
wherein the diameter of the stent comprises at least one of a proximal end diameter or a distal end diameter.

* * * * *